United States Patent [19]
Recigno

[11] Patent Number: 5,616,899
[45] Date of Patent: Apr. 1, 1997

[54] SYSTEM FOR MANAGING CASES IN DENTAL LABORATORY

[75] Inventor: David T. Recigno, Willow Grove, Pa.

[73] Assignee: Recigno Laboratories, Inc., Willow Grove, Pa.

[21] Appl. No.: 461,283

[22] Filed: Jun. 5, 1995

[51] Int. Cl.⁶ .................................................. G06F 17/00
[52] U.S. Cl. ........................... 235/375; 364/468.01
[58] Field of Search ................................. 235/375, 376; 364/401, 402, 468

[56] References Cited

U.S. PATENT DOCUMENTS

| | | | |
|---|---|---|---|
| 5,142,128 | 8/1992 | Perkin et al. | 235/375 |
| 5,376,777 | 12/1994 | Kamei et al. | 235/375 |
| 5,491,637 | 2/1996 | Kramer et al. | 235/375 |

OTHER PUBLICATIONS

"Catalog of Computer Software and Hardware", pp. 15–17, May 1995 edition of *LMT* (Lab Management Today), published by Dental Lab Publications, Inc.

*Primary Examiner*—Donald T. Hajec
*Assistant Examiner*—Jeffrey R. Filipek
*Attorney, Agent, or Firm*—Caesar, Rivise, Bernstein, Cohen & Pokotilow, Ltd.

[57] ABSTRACT

A system for managing the processing of dental appliances being fabricated in a dental laboratory. The fabrication of such appliances is achieved in a series of iterations, the first of the iterations occurring upon receipt of a prescription from the doctor for fabricating the appliance therefrom. Subsequent iterations occur upon return of the appliance by the doctor to the laboratory for additional processing. The system comprises a digital processing means, a data collection means, and data storage means. The data collection means is arranged to collect process related data associated with each iteration. The data storage means is arranged to store said process related data associated with each iteration while preserving previously stored data associated with prior iterations. Data indicative of the history of the fabrication of the appliance through all of the iterations is available to the operator of the laboratory for analysis and the effective and efficient management of the laboratory.

19 Claims, 19 Drawing Sheets

FIG. 9

Doctor — 110

- Doctor ID: [ ]  [?]  Terms: [ ▼ ]   Date: [ ]
- Last Name: [ ]   M.I.: [ ]
- First Name: [ ]   SS#: [ ]
- Lic Num: [ ]   Birth Date: [ ]
- Territory: [ ▼ ] [ ]
- Salesperson: [ ▼ ] [ ] [ ]
- Comments: [ ]

FIG. 10

Locations — 120

- Doctor ID: [ ] [🔍] [ ]
- Location ID: [ ▼ ]  Name: [ ]
- Address 1: [ ]
- Address 2: [ ]
- City: [ ]  State: [ ]  ZIP: [ ]
- Phone: [ ]  Fax: [ ]  Contact: [ ]  Carrier (ShipVia): [ ▼ ]
- Pickup/Delivery Preference: [ ]
- Vacations — Start Date: [ ]  End Date: [ ]   Stop Number: [ ]   [Business Hours] — 122
- Comments: [ ]

FIG. 11

Business Hours — 130

Location ID: [ ]  Name: [ ]

|  | Morning | | Afternoon | | PickUp |
|---|---|---|---|---|---|
|  | Open 1 | Close 1 | Open 2 | Close 2 | |
| Mon | | | | | ☐ |
| Tues | | | | | ☐ |
| Wed | | | | | ☐ |
| Thur | | | | | ☐ |
| Fri | | | | | ☐ |
| Sat | | | | | ☐ |
| Sun | | | | | ☐ |

Estimated Arrival Time: [ ]

FIG. 12

Territory — 140

Territory Code: [ ▼ ]  Driver: [ ]

Description:

Case Type Workstation Preferences — 170

Department Information
- Division ID: [ ▼ ]    Dept ID: [ ▼ ]

- Doctor ID: [  ] [?]
- Case Type: [ ▼ ]
- Process Type ID: [ ▼ ]
- Workstation ID: [ ▼ ]
- Preferences:
  [                    ]

FIG. 16

Products — 180

- Product Code: [ 🔍 ]    ☐ Serial # Required
- Description:
  [                    ]
- Product Class ID: [ ▼ ]
- Price: [  ]   Cost: [  ]   Type: [ ]
- Part Number: [  ]   Manufacturer: [  ]
- Billing Description:
  [                    ]
- Product Notes:
  [                    ]

FIG. 17

Billing Codes

Billing Code:

Percentage Charge:

Description:

FIG. 17A

Schedule Pickup/Delivery

Division ID: Doctor ID: Location ID: Last Name: First Name:

Delivery Only
Case ID: Rx ID:

Phone: Contact:

Date & Time: Territory: Carrier (Ship Via):

Est. Arrival Time: Req. Arrival Time: Status: Stop Num:

Pickup/Delivery Preferences:

Comments:

FIG. 18

Case Entry — 200

Case Information
- Doctor ID: [  ] [?]   Creation Date: [  ]
- Doctor Last Name: [  ]  Init. [  ]  First Name: [  ]  Phone: ( ) [  ]  Doctor Terms: [  ]
- Case ID: [  ] [?]   Patient Last Name: [  ]   First Name: [  ]
- Shade: [  ▼]   Mould: [  ▼]
- Case Comments:   Status: [▼] [  ]
- [              202              ]

Rx History
| Rx ID: | Receipt Date: | Ship Date: | Remake: |
|---|---|---|---|
|  |  |  |  |
|  |  |  |  |
|  |  |  |  |
|  |  |  |  |
|  |  |  |  |

- Rx Detail — 204
- Materials — 206
- Teeth — 208

FIG. 19

Tooth Indicator — 230

UPPER: 1–16 (Right / Left)
LOWER: 17–32 (Right / Left)

Tooth Comments:
[                              ]

[ Save ]   [ Cancel ]   [ Pontics ] □   [ Abutments ] □

FIG. 20

Rx Detail — 220

Case Information
- Case ID:
- Patient Name:
- Doctor ID:

Prescription Information
- Division ID:
- Prescription ID:
- Status:
- Remake — 232
- Delivery Loc:
- Receipt Date:
- Due Date:
- Dr's Due Date/Time
- Ship Date: — 212
- Pan Num: — 214
- Prescription Comments: — 218, 216

Scheduling — 220
- Case Type ID:
- Process Type ID:
- Schedule — 236
- Rx Image — 234

FIG. 21

Schedule — 240

Case/Prescription Information
- Case ID:
- Patient Name:
- Doctor ID:
- Prescription:
- Status:

Case Type Information
- Case Type:
- Process Type:
- Case Type Preferences/Comments:

Workstations
| Seq. | Workstat. | Description | Est. In | Act. In | Est. Out | Act. Out | Tech. ID |
|------|-----------|-------------|---------|---------|----------|----------|----------|
|      |           |             |         |         |          |          |          |
|      |           |             |         |         |          |          |          |

Workstation Preferences/Comments:

- Work Detail
- Print Labels — 242

FIG. 22A

Work Ticket
Label-1                                     248

| Doctor: | | Label #1 |
| Case ID: | Rx ID: | |
| Case Type: | Process Type: | |
| Division: | Department: | Pan No: |
| Created: | Receipt: | Due: |

Case Comments

Rx Comment

Material Comment

Case Type Preferences

Work Ticket
Label-2

FIG. 22D Rx Return Form

Return To:

Recigno Laboratories

Division:
Doctor:          Patient Name:
Case ID:
Rx ID:
Preferences

FIG. 22E Shipping Label

Recigno Laboratories, Inc.
Ship To:

Beaumont Hospital

Ship Via:
Territory:          Stop Number:
Doctor:
Doctor ID:          Location ID:
Case ID:

FIG. 23

Scan Maintenance — 280

Case ID: | ScanType: | Department: | Employee ID: | Date Range: | Search — 281

Scan Information

| ScanType | Date | Case ID | Scan Serial # | Department | Employee ID |
|---|---|---|---|---|---|
| | | | | | |
| | | | | | |
| | | | | | |
| | | | | | |
| | | | | | |
| | | | | | |
| | | | | | |

Detail

FIG. 24

Workstation Logging — 290

Division ID: | Case ID: | Rx ID: | Instance: | Sequence:

Case Type ID: | Workstation ID:

Act. In Date and Time: | Act. Out Date and Time:

Employee ID: | Last Name | First Name

Metal ID: | Weight: | Time Spent: — 291

SYSTEM FOR MANAGING CASES IN DENTAL LABORATORY

BACKGROUND OF THE INVENTION

This invention relates to systems for managing and analyzing the operation of a dental laboratory engaged in the fabrication of dental appliances, e.g., dentures, partial dentures, implants, crowns, bridges, and mouthguards at the prescription of a dentist to increase efficiency and maximize profitability.

Typically, a dental laboratory constructs any one of a variety of artificial dental structures or appliances, i.e., dentures, partial dentures, crowns and bridges, which serve to replace a patient's lost dentition in an aesthetically pleasing manner. These structures are commonly referred to as "cases" during their fabrication in a dental laboratory and are fabricated in accordance with a prescription provided by the dentist.

There are several systems presently available in the marketplace that automate certain aspects of the operation of a dental laboratory in the fabrication of the dental appliances or cases. However, these prior art systems leave much to be desired. Most importantly, these systems are concerned primarily with the record keeping functions of the dental laboratory and often do little more than automate the generation of invoices sent to the dentists prescribing the appliances. Because these presently available systems are geared toward the limited functions of record keeping, they are arranged to gather only the information relating to a case that is necessary for generating bills.

These presently available systems do not provide a means for tracking cases from pickup at the prescribing dentist's office through laboratory production steps to delivery and invoicing. These systems do not provide a means for keeping track of important historical information about cases for the purpose of increasing efficiency in a dental laboratory. By historical information it is meant all information relating to the processing of a case from the time the case is originated in the dental laboratory to the time of completion of the dental appliance. Typically, under systems presently available, information relating to the processing of a case is overwritten each time the case is returned to the dental laboratory for further processing and therefore no historical record is created. Additionally, these systems deal primarily with record keeping functions and do not provide analytical tools that increase efficiency and productivity and streamline the process flows of the dental laboratory. Also, present systems deal primarily with single location dental laboratories, and do not possess the ability to handle dental laboratory enterprises comprising more than one main division and/or a plurality of auxiliary divisions.

The system of the present invention is geared to the process or manufacturing aspect of the dental laboratory business as well as record keeping. Therefore, it is capable of providing a significant amount of detailed and useful information regarding the process side of the dental laboratory business that is unavailable on presently existing systems. Because the system of the present invention considers so much detailed information relating to the processing of cases in a dental laboratory, it provides an analytic capability previously unavailable on other systems.

Specifically, the system of the present invention gathers and archives pertinent information regarding processing of cases in a dental laboratory including driver routing information necessary for case pickup, information relating to the laboratory, division and department where the work will be performed on that case, the process steps to be performed on that case, the workstations at which work will be performed, the identity of the technicians performing those steps, the elapsed time to perform process steps, number of iterations for each case, and doctor's preferences, the status of a case and other useful information. Additionally, the dental laboratory can advise doctors who have work pending in the dental laboratory when they can expect their cases back.

Because the system of the present invention is geared to the processing and data storage aspect, it provides a means for tracking cases from pickup through laboratory processing steps to delivery and invoicing. The system of the present invention also serves as an analytical tool that may be utilized by management to analyze collected data for the purpose of improving productivity and efficiency and containing costs through scientific management techniques. For example, using the information gathered by the system of the present invention, dental laboratory management can determine which doctor's cases are being worked on longest by laboratory technicians and which laboratory technicians consume the most time to finish work.

OBJECTS OF THE INVENTION

It is a general object of this invention to provide a computerized system for managing cases in a dental laboratory which overcomes the disadvantages of the prior art.

It is another object of this invention to provide an automated system for tracking cases in a dental laboratory from pickup, through laboratory processing steps to delivery and invoicing.

It is another object of this invention to keep track of historical information for the purpose of increasing efficiency in the operation of a dental laboratory.

It is another object of this invention to minimize errors associated with automated case management systems through the use of bar-code printers and hand-held scanners.

It is another object of this invention to increase the speed of processing of dental laboratory orders.

It is another object of this invention to streamline the process flows associated with a dental laboratory.

It is another object of this invention to increase the level of service offered by a dental laboratory.

It is another object of this invention to provide accurate and timely management information in order to increase efficiency.

It is another object of this invention to reduce the workload and manpower requirements associated with the operation of a dental laboratory.

It is another object of this invention to provide a computerized system for managing cases in a dental laboratory wherein said dental laboratory has multiple divisions.

SUMMARY OF THE INVENTION

These and other objects of this invention are achieved by providing a system for managing and analyzing the operation of a dental laboratory engaged in the fabrication of dental appliances such as dentures, partial dentures, implants, crowns, bridges and mouthguards at the prescription of a dentist.

Fabrication of these appliances is achieved in a series of iterations, with the first of these iterations occurring upon receipt of a prescription from the doctor for fabricating an appliance. Subsequent iterations include the return of the appliance by the doctor to the laboratory for additional processing steps including try-in, finish, etc.

The system of the present invention comprises digital processing means, data collection means, and data storage means. In the preferred embodiment, the digital processing means comprises a plurality of microcomputers located in various departments within the dental laboratory that are linked in a network arrangement.

The data collection means, e.g., portable, hand-holdable bar-code scanners, is arranged to collect process related data associated with each iteration during the fabrication of each appliance.

The data storage means, e.g., a relational database, is arranged to store the collected process related data associated with each iteration while preserving previously stored data associated with prior iterations. The system of the present invention makes available to dental laboratory personnel data indicative of the history of the fabrication of the appliance through all of the iterations. This information can be utilized by dental laboratory personnel for analysis and for the effective and efficient management of the laboratory.

DESCRIPTION OF THE DRAWINGS

FIG. 9 is an illustration of one particular screen display, i.e., the Doctor Form screen display, produced by the software forming a portion of the present invention;

FIG. 10 is an illustration of one particular screen display, i.e., the Locations Form screen display, produced by the software forming a portion of the present invention;

FIG. 11 is an illustration of one particular screen display, i.e., the Business Hours Form screen display, produced by the software forming a portion of the present invention;

FIG. 12 is an illustration of one particular screen display, i.e., the Territory Form screen display, produced by the software forming a portion of the present invention;

FIG. 13 is an illustration of one particular screen display, i.e., the Ship Via Form screen display, produced by the software forming a portion of the present invention;

FIG. 14 is an illustration of one particular screen display, i.e., the Case Type Preferences Form screen display, produced by the software forming a portion of the present invention;

FIG. 15 is an illustration of one particular screen display, i.e., the Case Type Workstation Preferences Form screen display, produced by the software forming a portion of the present invention;

FIG. 16 is an illustration of one particular screen display, i.e., the Product Code Form screen display, produced by the software forming a portion of the present invention;

FIG. 17 is an illustration of one particular screen display, i.e., the Billing Code Form screen display, produced by the software forming a portion of the present invention;

FIG. 17a is an illustration of one particular screen display, i.e., the Schedule Pick-up and Delivery Form, produced by the software forming a portion of the present invention;

FIG. 18 is an illustration of one particular screen display, i.e., the Case Entry Form screen display, produced by the software forming a portion of the present invention;

FIG. 19 is an illustration of one particular screen display, i.e., the Tooth Indicator Form screen display, produced by the software forming a portion of the present invention;

FIG. 20 is an illustration of one particular screen display, i.e., the RX (prescription) Detail Form screen display, produced by the software forming a portion of the present invention;

FIG. 21 is an illustration of one particular screen display, i.e., the Schedule Form screen display, produced by the software forming a portion of the present invention;

FIG. 22A is a pictorial representation of a portion of the work ticket used in accordance with the present invention;

FIG. 22D is a pictorial representation of a shipping label used in accordance with the present invention;

FIG. 22E is a pictorial representation of an RX (prescription) return form used in accordance with the present invention;

FIG. 23 is an illustration of one particular screen display, i.e., the Scan Maintenance Form screen display, produced by the software forming a portion of the present invention;

FIG. 24 is an illustration of one particular screen display, i.e., the Workstation Logging Form screen display, produced by the software forming a portion of the present invention;

DETAILED DESCRIPTION OF THE PREFERRED EMBODIMENTS

Figure 1:
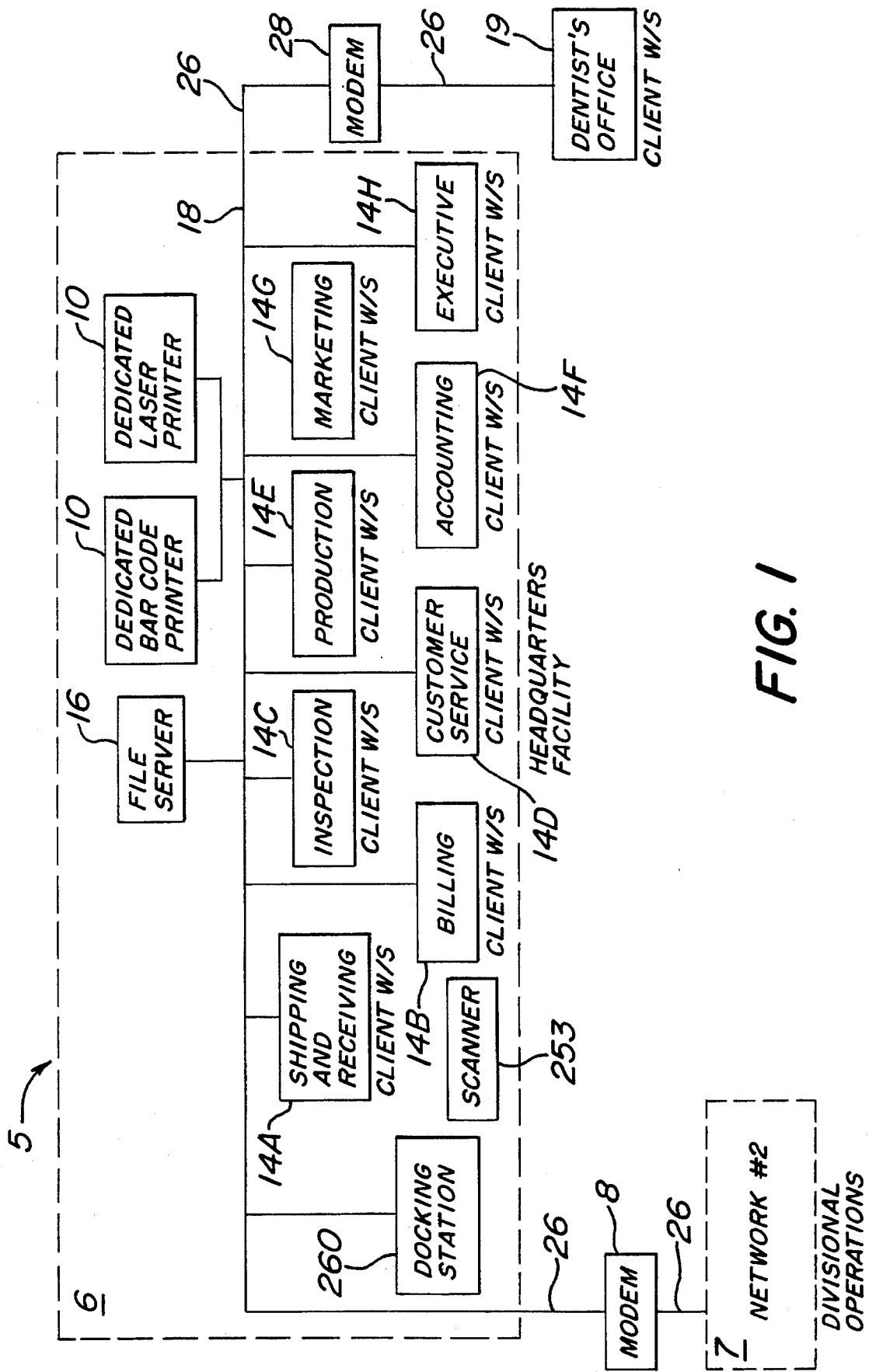
FIG. 1 is a block diagram of a distributed data processing system for managing and analyzing the operation of a dental laboratory in accordance with the present invention.

Referring now to various figures of the drawings where like reference numerals refer to like parts, there is shown in FIG. 1, an embodiment of the dental laboratory case management system 5 constructed in accordance with this invention.

As is seen in FIG. 1 the dental laboratory case management system 5 comprises a plurality of networks 6 and 7, said networks being connected by means of telephone lines 26 and a modem 8. Two networks, 6 and 7 are depicted in FIG. 1 for purposes of illustration. It should be understood that the system 5 of the present invention can be implemented as a single network in a dental laboratory having a single location and, alternatively, can be implemented as a plurality of any number of networks where the dental laboratory comprises many divisions, one network being located within one division and linked to other networks located at other divisions by means of telephone lines 26 and modems 8. Each network enables users on that network to share data stored on disks and files and to share hardware devices such as laser printers 10 located on that network in a manner that is known to those practiced in the art.

Still referring to FIG. 1, in the preferred embodiment described herein, each of the networks of the system 5 of the present invention is organized in an arrangement known by those practiced in the art as the client/server architecture. Under the client/server architecture each network in system 5 comprises three components including a plurality of client workstations, e.g., 14A through 14H, a server 16 and a communications channel 18. Those practiced in the art are aware that under the client/server architecture, computing tasks are evenly divided between the database server 16 and the plurality of client workstations, e.g., 14A through 14H, to provide a high level of performance, productivity and cost effectiveness.

In the preferred embodiment, network 6 of system 5 comprises eight client workstations 14A through 14H located in and corresponding to various departments of the dental laboratory. As shown in FIG. 1, a client workstation 14A is located in the shipping and order entry department, a client workstation 14B is located in the billing department, a client workstation 14C is located in the inspection department, a client workstation 14D is located in the customer service department, a client workstation 14E is located in the production department, a client workstation 14F is located in the accounting department, a client workstation 14G is located in the marketing department, and a client workstation 14H is located in the executive offices for use by management. There is also shown a client workstation 19 located remotely at a dentist's offices (to be discussed in further detail later in this disclosure).

Figure 2:
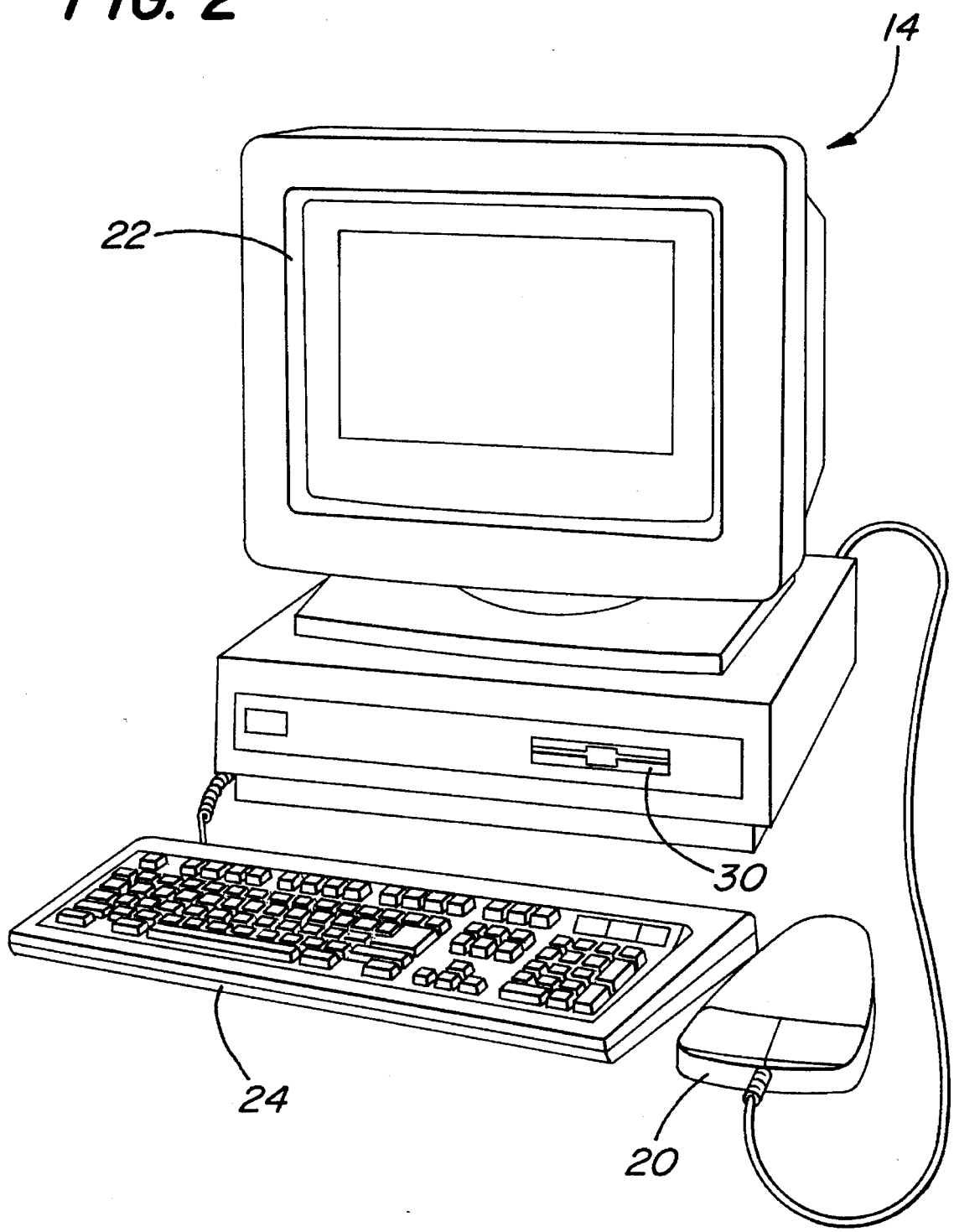
FIG. 2 is an isometric view of one workstation forming a portion of the system of the present invention.

Referring now to FIG. 2, there is depicted any one of the plural client workstations utilized in any one of the networks of the system 5 of the present invention. Each client workstation serves as the interface between the system 5 and the user. The client workstation is often a microcomputer, e.g., personal computer. Microcomputers utilized as workstations, e.g., 14A through 14H, in system 5 preferably possess an 80486 type microprocessor or faster and between eight and sixteen megabytes of random access memory along with a mouse pointer 20, a high-quality color monitor 22 and a high-quality keyboard 24.

In the preferred embodiment of the present invention, each of the client workstations 14A through 14H may be equipped with any one of several operating systems that enables the client workstation to communicate with other workstations in the network and the server 16. Additionally, the operating system of each client workstation provides a graphical user interface (GUI) that enables users to interact with the client workstation by means of a group of icons located on a bar at the top of the screen. These icons are selected by the user by means of utilizing a mouse pointer. One such product designed to be utilized by client workstations in the client/server architecture and having both the networking and operating system capabilities described above is sold under the name WINDOWS FOR WORKGROUPS by Microsoft Corporation. WINDOWS is a trademark of Microsoft Corporation.

The server 16 of each network of system 5 is an unattended microcomputer, e.g., personal computer, preferably equipped with an 80486 microprocessor or faster or any other microprocessor which will be compatible with the operating system and a random access memory comprising sixteen or more megabytes. Under the client/server architecture, each server 16 communicates with the client workstations, e.g., 14A through 14H, within the server's network 6 and honors requests submitted by the client workstations, e.g., 14A through 14H, for file operations such as printing, opening and closing files and writing to files. The server 16 provides the client workstations with shared access to disks, files and printers. The server 16 may be equipped with any one of several operating systems that enable it to communicate with the client workstations, e.g., 14A through 14H. One such operating system is sold under the name WINDOWS NT ADVANCED SERVER by Microsoft Corporation. WINDOWS NT is a registered trademark of Microsoft Corporation.

Additionally, the client/server architecture as disclosed in the present invention exploits the benefits of a relational database that is resident on the server 16 wherein information is stored in tables and formed into relationships using links in a manner familiar to those practiced in the art. The server 16 is provided with any one of several software packages that enables users to enter, edit and retrieve data from the relational database in response to requests from clients. One such relational database management system software package particularly suited to perform these tasks is sold under the name MICROSOFT SQL SERVER by Microsoft Corporation.

Each network of system 5 provides a communications channel 18 between each of the client workstations, e.g., 14A through 14H and the server 16. The communications channel 18 consists of hardware including network adapter cards (not shown), hub (not shown), cables (not shown) and software such as a network operating system that enables the transmission and receipt of data among all the client workstations, e.g., 14A through 14H, and servers 16 within respective networks, 6 and 7. Software and hardware particularly suited to perform the networking task is sold under a variety of names, including ETHERNET (™) by Xerox Corporation.

The system 5 is to be implemented by a dental laboratory business comprising one or several divisions. Typically, in the multi-divisional dental laboratory, the headquarters operates at one location and one or more divisions operate at remote locations. System 5 is to be utilized by these multi-locational dental laboratory divisions by implementing one network 6 described herein at the headquarters facility of the dental laboratory to serve as the main network and connecting that network 6 to one or more additional networks, e.g., 7, implemented at each of the divisional operations. Linking of these networks, e.g., 6 and 7, is implemented by means of conventional modems 8 and telephone lines 26 in a manner that is familiar to those practiced in the art. One such software package particularly suited to linking networks together by means of modems and telephone lines is known as Remote Access Services. Remote Access Services is a feature offered under the previously mentioned WINDOWS NT ADVANCED SERVER by Microsoft Corporation. Additionally, as shown in FIG. 1, the invention of the present application is intended to be utilized in a manner that enables a doctor, e.g., dentist, periodontist, endodontist, to obtain relevant information from the system remotely by means of a client workstation 19, e.g., personal computer, located in the doctor's office and connected to the system 5 through telephone lines 26 and a modem 28.

Referring again to FIG. 2 there is depicted a pictorial representation of the video display of one of the client workstations 14 of the present invention.

For initial set-up of each of the client workstations, e.g., 14A through 14H, in the system, the user inserts one or several diskettes containing workstation source code in slot 30 of the client workstation and is presented with a screen display (not shown) prompting the user to input certain information by means of the keyboard 24 and mouse pointer 20 to enable copying of the application software package from the diskettes onto the permanent memory of the workstation. This set-up procedure is repeated by the user for each client workstation, e.g., 14A through 14H, in the system 5.

Similarly, for initial set-up of each of the servers 16 in the system 5, the user inserts one or several diskettes containing server source code of the system 5 in the slot of the database server 16 and is presented with a screen display (not shown) prompting the user to input information by means of the keyboard 24 and mouse pointer 20 to enable copying of the application software package from the diskettes onto the permanent memory of the server. This set-up procedure is repeated by the user for each server 16 in the system 5. In the preferred embodiment, the application software of the present invention can be written in any one of a number of suitable programming language products sold under various trademarks. Two such programming language products are particularly suited for the system of the present invention. One is sold under the Registered Trademark VISUAL BASIC and the other is sold under the Registered Trademark VISUAL C++, both by Microsoft Corporation.

When the set-up procedure has been completed, the software generates an icon (not shown) on the screen display of monitor 22. When the icon is selected by double-clicking the mouse pointer button 20, the system 5 prompts the user for a group of inputs enabling the user's access to a client workstation, e.g., 14A through 14H, at which the user is located and access the server 16.

Referring again to FIG. 1, the system 5 of the present invention is equipped with various security levels to maintain the integrity of the database resident on the server 16 within each network. In other words, only designated personnel have access to all aspects of the system 5 including the ability to input and modify information in the database. On the other hand, doctors who access the system 5 by means of a client workstation 19 connected to the system 5 by means of modom 28 and telephone lines 26 have only limited access to the system 5, i.e., they are only able to view data and not modify or add data, except to schedule pick-ups of cases from their office(s) and to add their "preferences", e.g., that crowns be prepared with a stippled rather than smooth finish. The designation of doctor preferences and scheduling pick-ups are features of the system of the present invention which will be discussed in detail later.

The case management system 5 of the present invention enables system users to effectively manage the various steps involved in the processing of cases in a dental laboratory from case origination through fabrication of the final dental appliance. Additionally, the case management system of the present invention enables dental laboratory management to perform analytical functions such as the determination of labor costs by calculating process times at various workstations and keeping track of iterations, i.e., the number of times a case is returned by a doctor to the laboratory for additional processing.

The fabrication of a dental prosthetic appliance, i.e., a case, can best be described as an iterative process sometimes involving a few and more often times involving many steps depending upon a variety of factors. That is, when a dental prosthetic appliance created by the laboratory is initially fitted into the patient's mouth, it is usually necessary for the dentist to return that appliance to the dental laboratory for further processing one or several times before that appliance is formed to achieve a suitable fit within the patient's mouth.

For example, a dentist may recognize that a patient will benefit from the use of a full upper and full lower denture. The dentist will first create impressions of the patient's upper and lower dentition by using two dental impression trays. Each dental impression tray is loaded with a suitable setting impression material. The first dental impression tray is utilized for creating an impression of the patient's upper dentition and the second dental impression tray is utilized for creating an impression of the patient's lower dentition. Each of the two dental impression trays is loaded with impression material and sequentially positioned within the patient's mouth. The patient bites into the impression material contained within each tray to form an impression of the upper and lower dentition in the patient's mouth.

After the material sets, the doctor sends the upper and lower impressions to the dental laboratory with a set of instructions, commonly referred to as an "RX" or prescription, to fabricate a "wax-up" denture based upon these impressions. It is important to note that receipt by the dental laboratory of the RX or prescription along with these impressions from the doctor's office is considered to be the first "iteration" in the processing of the case.

There are several steps involved in the fabrication of the wax-up denture. First, upon receipt of the impression trays from the doctor's office, a technician in the dental laboratory pours stone or plaster into the impression trays to create two plaster models. Each of these plaster models is used to create the dental prosthetic device that will be placed into the patient's mouth to replace and simulate missing dentition.

The first plaster model represents a positive impression of the patient's existing upper dentition. This plaster model shows the shape and position of the patient's existing upper teeth and also shows where upper teeth are missing. Likewise, the second plaster model represents a positive impression of the patient's lower dentition. The second plaster model shows the shape and position of the patient's existing lower teeth and also shows where lower teeth are missing.

Once these plaster models are created, a step known as "articulation" is performed. In articulation, the dental laboratory technician places the two plaster models of the upper and lower dentition into a device commonly known as an "articulator". Once placed into the articulator, the technician can adjust the upper and lower plaster models to achieve proper occlusion, i.e., proper relationship of the surfaces of the upper and lower teeth when in contact with one another.

Once the plaster models have been articulated and proper occlusion has been achieved, a step known as "set-up" is performed. During set-up, the dental laboratory technician selects artificial teeth made from acrylic or porcelain and using set-up wax, roughly places the artificial teeth in the upper and/or lower plaster models at positions where the patient has lost teeth. Set-up is performed while the upper and lower plaster models remain positioned in the articulator. Again using the articulator to simulate the opening and closing of the mouth, the technician determines that proper occlusion is achieved with the selected artificial teeth positioned in the plaster models.

Next, a step known as "wax-up" is performed. In wax-up, a technician carefully applies wax over the artificial teeth in their set-up position while in the articulator so as to create a wax-up denture. The wax-up denture consists of the artificial teeth held in their positions by the wax. This is the resulting wax-up denture that is returned to the doctor for a trial fitting within the patient's mouth.

In particular once the doctor has received the wax-up, he/she will place the device in the patient's mouth. This step is known as the first "try-in". After observing the wax-up in the patient's mouth, the dentist may determine that artificial teeth in the wax-up denture must be repositioned by the dental laboratory. The doctor may deem it necessary to make several other types of changes to the wax-up. If the doctor deems that changes are necessary, he/she will return the case to the dental laboratory with a prescription to make further modifications in order to perform a second try-in in order to achieve a better fit. It is important to note that receipt of the wax-up by the dental laboratory with another prescription from the doctor is regarded as the second iteration in the creation of the denture.

Many times, the doctor will determine that a third, fourth or fifth try-in is necessary to assure a proper fit within the patient's mouth. Each time the doctor returns the denture to the laboratory with a prescription for further adjustments, another iteration occurs requiring additional processing steps to be performed in the dental laboratory.

Once the doctor is satisfied that the wax-up fits suitably within the patient's mouth, he/she returns it to the laboratory with another prescription instructing the laboratory to make the final denture. This adds another iteration in the processing of the case. To finish the denture, the laboratory performs the step of "investing". This step involves the placement of plaster around the wax portions of the wax-up denture and placing the resulting product into a flask. A "boil-out" step is then performed, whereby the wax is boiled away. Next, the denture is packed with acrylic in a flask, cured under a heat polymerization system, and "devested" i.e. removed. Next, the rough acrylic is finished with a finishing bur, then polished to put a high shine on the denture. Finally, the denture is disinfected.

Thereafter, the denture is returned to the doctor as the final denture. If the doctor is satisfied with the fit of the finished denture within the patient's mouth, no further iterations are necessary.

It is not unlikely that a particular case could go through as many as ten iterations or more before being completed to the doctor's satisfaction. Since many dental laboratories charge a fixed amount for the preparation of various dental appliances, regardless of the number of iterations needed to complete the case, as the number of iterations for a particular case increases, labor and material costs increase and therefore profit made by the dental laboratory on the case decreases. Thus, doctors who return a given case to the laboratory for further processing a number of times that is above average create higher costs for the laboratory and thereby decrease the laboratory's profits.

Therefore, in order to minimize costs and thereby increase efficiency and profit, it is in the dental laboratory's best interest to identify those cases where excessive iterations have occurred and determine how to eliminate these occurrences in the future. The case management system 5 of the present invention enables dental laboratory management to do just this by recording and archiving the number of iterations for each particular case being processed. That is, if an unusually high number of iterations are detected for a particular case, this may indicate that a particular technician requires further training or that a doctor has been returning cases where work has been satisfactorily been performed.

With each additional iteration, the system 5 of the present invention collects and archives a wide range of process information related to that specific iteration. Such process related information includes, but is not limited to, the identification of the technician who worked on the case during that iteration, the type(s) of process(es) performed, the division, department(s) and workstation(s) wherein these processes were carried out, the date, start time, finish time and elapsed time for performing each process step, prescription information, and doctor information such as name, telephone number, preferences and office hours.

As previously stated, prior art dental laboratory systems are geared primarily toward the function of record keeping. Therefore, under these prior art systems, all valuable historical information relating to the processing of cases is overwritten each time the case is returned to the dental laboratory for further processing. Conversely, under the system 5 of the present invention, the database retains all historical process related information relating to each iteration in the life of a case. This information remains resident in the system's database after the case has been completed and can be utilized by dental laboratory management in a number of different ways. In other words, under the present system 5, all process related information is preserved.

By collecting and storing information relating to each iteration in the lifecycle of a case, a comprehensive database or data warehouse of important process-related information is amassed. This information can be utilized by laboratory management in a number of different ways. Moreover, the laboratory management can utilize the .system 5 of the present invention to generate any one of various reports, e.g., comparative reports, historical reports, time based reports.

For example, utilizing said process-related information, a report can be generated to compare a selected group of technicians on the basis of elapsed time spent in completing jobs. Another report can be generated to compare a selected group of technicians on the basis of number of quality control rejections. Another report can be generated to compare doctors on the basis of number of times cases are returned to the laboratory for further processing. Another report can be generated to compare particular doctors on the basis of time taken before returning cases to the laboratory for further processing.

Essentially, information collected and retained within the database of the system of the present invention can be manipulated in any one of a myriad of ways to generate reports summarizing desired information. Further, information contained within the database can be utilized by dental laboratory management to determine labor and material costs so as to develop costing and pricing models for each specific dental laboratory operation.

To utilize the system 5 of the present invention, users perform three general functions: maintenance, processing of dental laboratory cases, and the generation of reports utilizing gathered process related information for use by management.

Under the maintenance function, the user adds records to the database and establishes logical relationships between these records by inputting data into a series of system generated forms. By inputting information during maintenance, said information is established on the system 5 and does not have to be retyped into the system 5 during the day-to-day processing of cases in the dental laboratory.

On forms to be discussed in detail below, the system prompts the user to assign unique identification numbers for various parameters within the database during maintenance, e.g., divisions, departments, case types, prescriptions, process types, workstations, doctors, locations, employees, territories, shippers, and associate descriptive information with those unique identification numbers.

For example, where a dental laboratory comprises multiple divisions located in different cities a user may choose to designate the identification of the various divisions based upon an abbreviated form of the city in which the division is located. For example, the code WG may designate the Division ID (identification) for a division located in Willow Grove, Pa. The code PL may designate the Division ID (identification) for a division located in Pleasantville, N.J.

Likewise, Department ID's (identifications) may be based upon an abbreviation of the department description. For example, RECV could be used to designate the Department ID (identification) for the receiving department and ARTIC may be used to designate the Department ID (identification) for the articulation department.

The system 5 automatically assign Case IDs (case identification) for each of the various cases processed in the dental laboratory. The system also prompts the user to input Workstation ID's (identifications) for the various workstations located within each of the departments. By way of example, typical Workstation ID's include RECV for receiving, ARTIC for articulation, WAX-UP for wax-up, FINSH for finishing, PORBLDUP for porcelain build-up, QC for quality control, PORGLAZE for porcelain glaze and SHIP for shipping.

The related database records that are established during the maintenance function are utilized on a daily basis during the processing function to be described in detail below. Because data relationships have been established during the maintenance function, the processing of transactions steps is expedited in ways to be described later in this specification, To aid in the describing the nature and content of the maintenance function of system 5, a walk-through of the various forms that appear on the display screen of the client workstation during use of the maintenance function follows.

A user wishing to review, update or add information to the system database can do so by selecting the Maintenance option from a system generated main menu bar. The system then displays a list of all forms under the maintenance function. The user selects a form from this listing utilizing the mouse pointer 20.

The function and operation of several of the forms under the maintenance option will be described in detail below.

Figure 3:
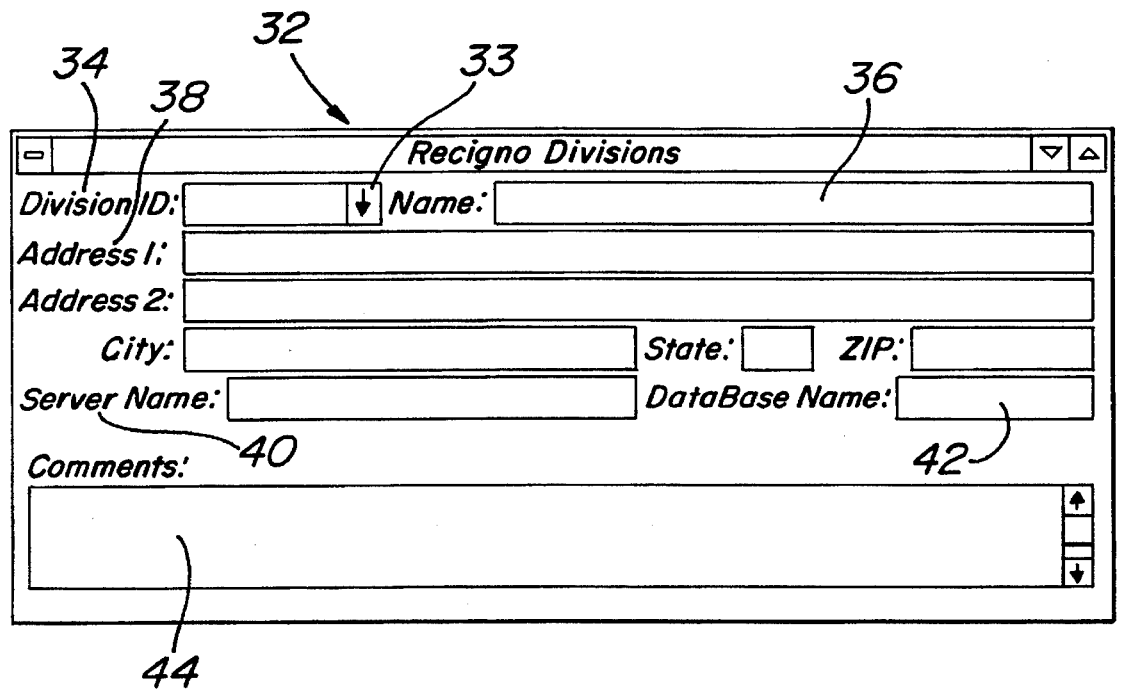
FIG. 3 is an illustration of one particular screen display, i.e., the Division Form screen display, produced by the software forming a portion of the present invention.

The Division Form 32 is displayed as shown in FIG. 3. In accordance with the present invention, the purpose of the Division form 32 is to enable the user to create and maintain within the database information relating to particular divisions that comprise a multidivisional dental laboratory. As shown in FIG. 3, the Division form 32 provides a plurality of fields, each field pertaining to a particular attribute of that division, e.g., Division ID (identification) 34, division name 36, division address 38, the name of the server 40 resident at that Division, and the identity of the database 42 resident at that division. Additionally, a comment box 44 is provided on the Division Form 32 to enable the user to insert comments about that division. By inputting the requested data on this form, the user establishes links between information relating to divisions within the lab.

To create new divisions within the database, the user clicks on the NEW button (not shown) on the command ribbon of the operating system and enters the information in the appropriate fields of the Division Form 32. Other forms in the system similarly utilize the NEW button on the command ribbon to create new records and the drop-down buttons located on the various forms for reviewing and updating existing records.

Once the Division Form 32 has been completed with respect to one or more divisions within the dental laboratory, the user can review and revise information about any of the previously inputted divisions. By clicking on the drop down button 33 located to the far right of the field labelled Division ID 34, the system 5 displays a list of division identifications previously inputted, each division identification representing a separate division that has been previously created by the user in the database. By clicking on any one of these displayed division identifications, the system enters that division into the Division ID field and populates all of the other fields on the Division Form 32 with information retrieved from the database relating to that particular division. In this manner, information about particular divisions can be reviewed, and updated as needed.

Figure 4:
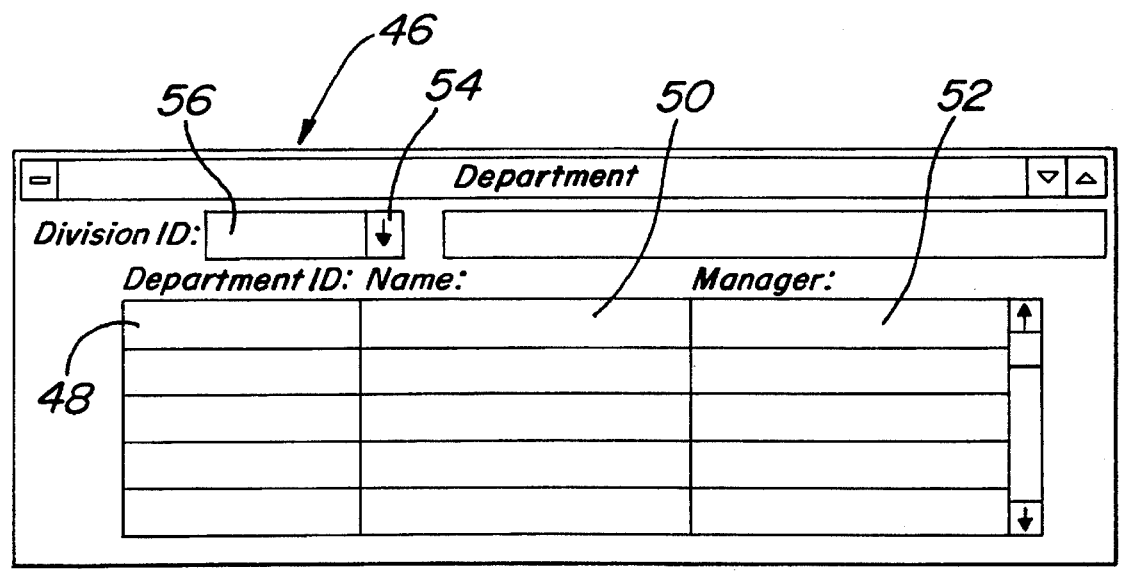
FIG. 4 is an illustration of one particular screen display, i.e., the Department Form screen display, produced by the software forming a portion of the present invention.

The Department Form 46 is displayed as shown in FIG. 4. In accordance with the present invention, the purpose of the Department Form 46 is to enable the user to create, update and review information relating to each department within each division of the dental laboratory. Fields are provided to record this related information including department identification 48, department name 50 and the name of the manager supervising that department 52. Typical departments found in a dental laboratory include shipping, receiving, acrylic, porcelain crown/bridge, metal, orthodontics, implants, administration, inspection, billing, etc. The user may create new departments in the system by utilizing the NEW button located on the command ribbon and entering information into the appropriate fields as previously described. The user can review and update existing department records by clicking on the drop-down button 54 located to the right of the Division ID field 56 and then clicking on any of the displayed division identifications, the system 5 enters that division identification into the Division ID field 56 and populates the rest of the fields on the form with information retrieved from the database.

Figure 5:
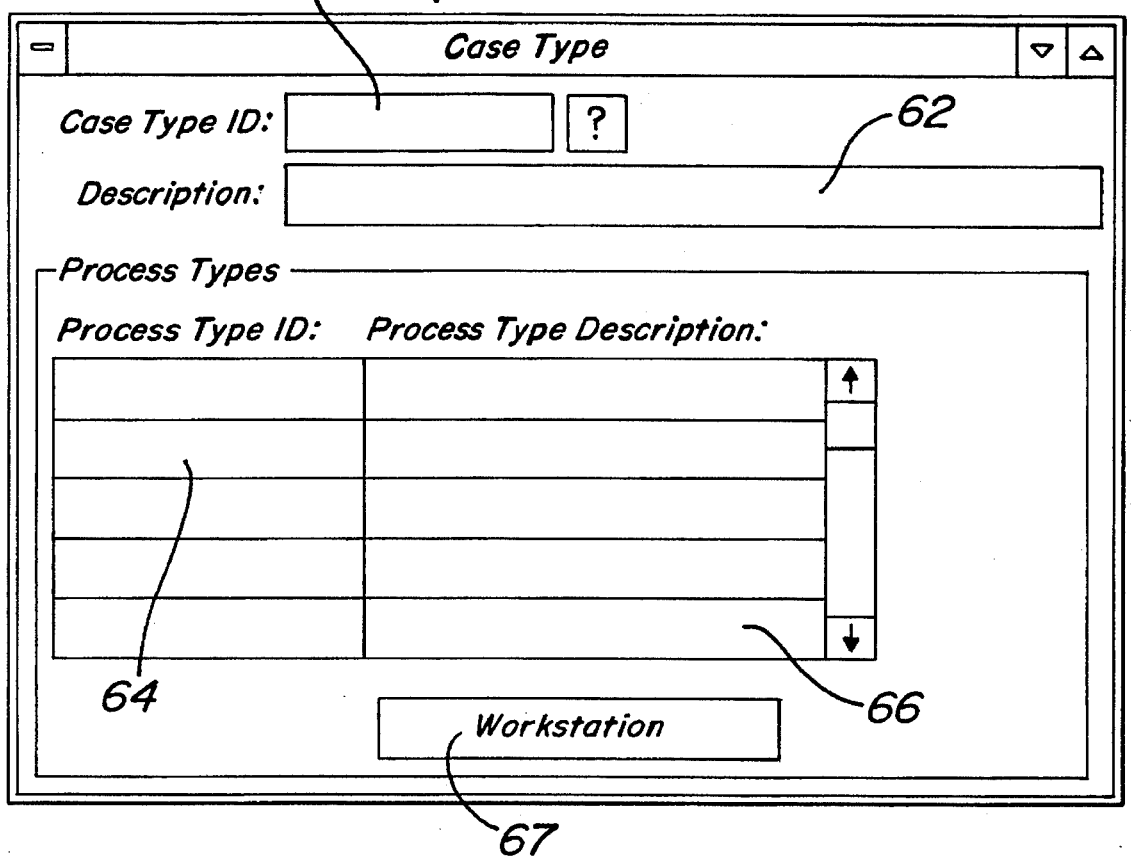
FIG. 5 is an illustration of one particular screen display, i.e., the Case Type Form screen display, produced by the software forming a portion of the present invention.

The Case Type Form 58 is displayed as shown in FIG. 5. A case type refers to any one of the many different types of dental appliances fabricated in a dental laboratory, e.g., dentures, partial dentures, implants, crowns and mouth guards. In the Case Type Form 58, the user enters information into fields about a new case type or updates and/or review information about existing case types. Fields are provided to input case type identification 60, case description 62, e.g., denture, partial denture, mouth guard.

The Case Type Form 58 also provides fields for Process Type ID 64 and Process Type Description 66. A process type includes all of the process steps performed at workstations between iterations in a particular case. For example, one process type referred to as finish denture to first try-in stage includes all of the workstations at which work is performed to prepare the wax-up denture for the first try-in, i.e., receiving, tooth selection, articulation, set-up, wax-up, quality control and shipping. A second process type, referred to as return from try-in, make changes for second try-in, includes all of the workstations at which work is performed to prepare the denture for the second try-in, e.g., set-up and wax-up workstations. A third process type, referred to as return from try-in and finish denture, includes all of the workstations at which work is performed to prepare the final denture, e.g., investing, boil-out, packing, curing, divesting, finishing, polishing, disinfecting, inspection and shipping. As previously stated, each process type has an associated Process Type ID 64 and Process Type Description 66. These attributes are inputted into the database on the Case Type form 58.

Figure 6:
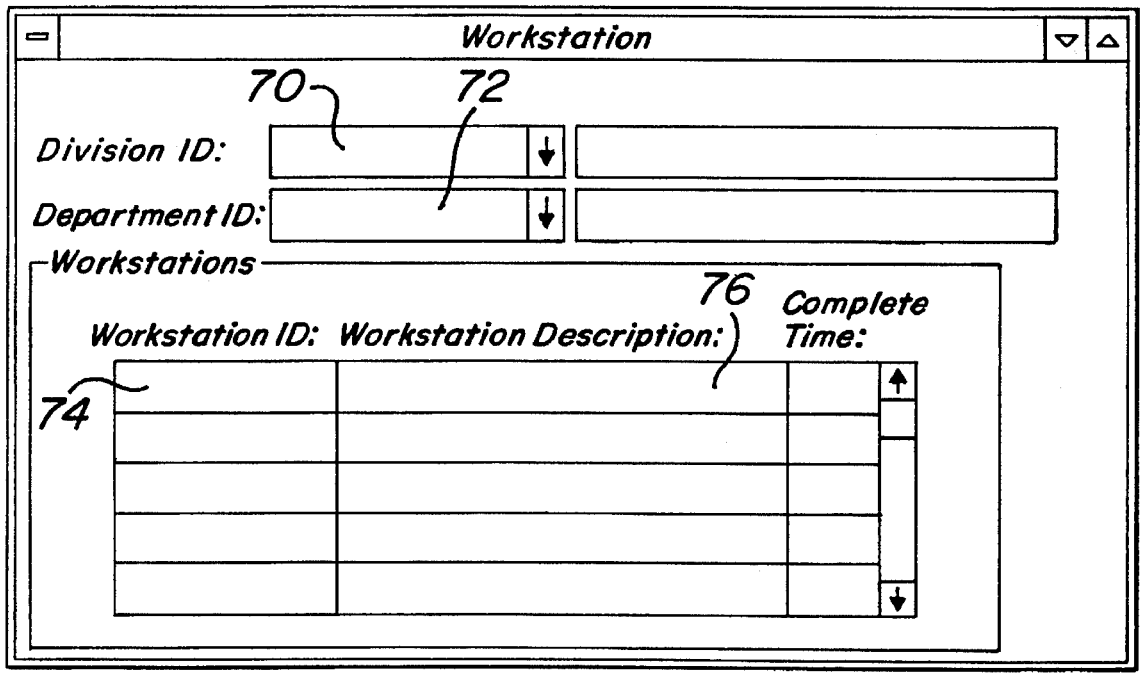
FIG. 6 is an illustration of one particular screen display, i.e., the Workstation Form screen display, produced by the software forming a portion of the present invention.

By depressing the Workstations Button 67 located at the bottom center of the Case Type Form 58, the user can gain access to the Workstations Form 68. The Workstations Form 68 is displayed as shown in FIG. 6. In accordance with the present invention, the purpose of the Workstations Form 68 is to enable the user to enter information relating to the identification and description of each of the various workstations within a department in the dental laboratory. These dental laboratory workstations are to be distinguished from the workstations previously discussed in this application in connection with client/server architecture. Fields are provided on the Workstations Form 68 including Division ID 70, Department ID 72, Workstation ID 74 and Workstation Description 76. Typically, workstations within the dental laboratory are manned by skilled technicians that perform specific processes on cases sent to the dental laboratory by doctors. As previously stated, typical workstations include RECV for receiving, ARTIC for articulation, WAX-UP for wax-up, SET-UP for set-up, FINSH for finishing, QC for quality control, PORGLAZE for porcelain glaze and SHIP for shipping.

Figure 7:
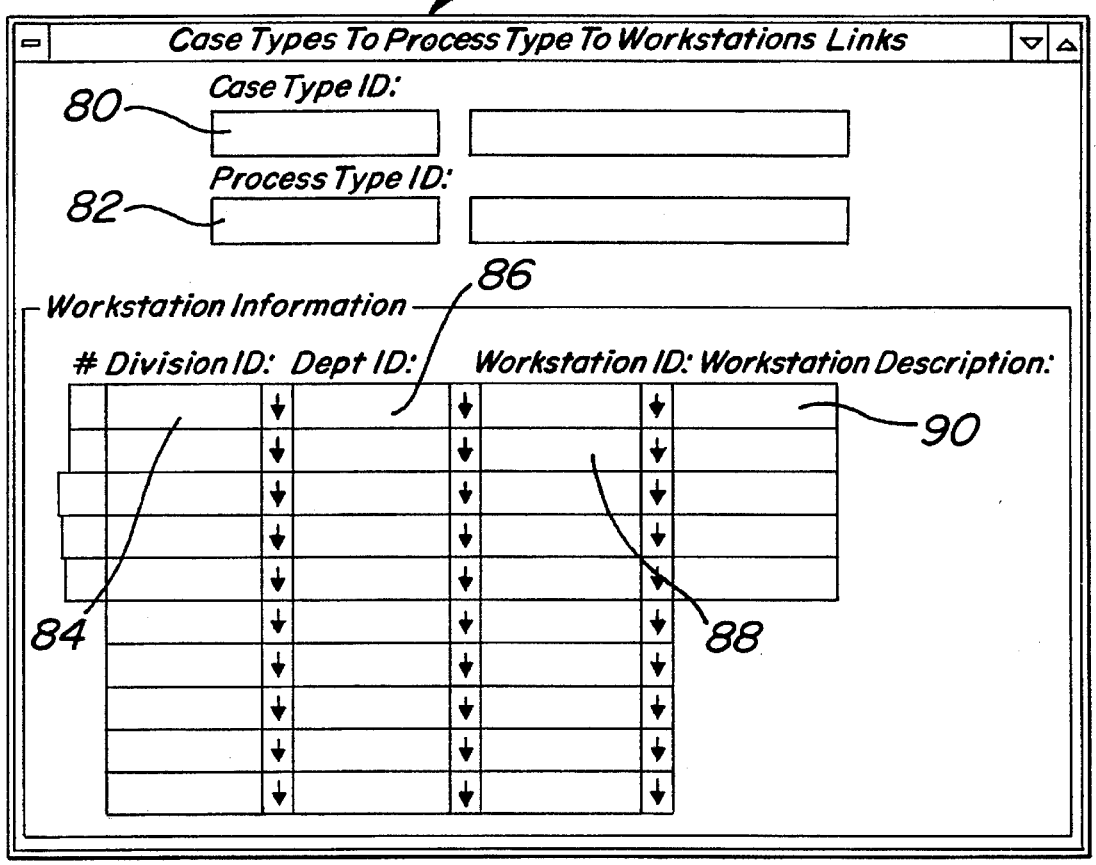
FIG. 7 is an illustration of one particular screen display, i.e., the Case Types To Process Types To Workstations Links screen display, produced by the software forming a portion of the present invention.

Relationships between particular case types, e.g., dentures, their related process types, e.g., first try-in, and the multiple workstations corresponding to each process type is established in the database through the use of the Case Type To Process Type To Workstation Links Form 78 shown in FIG. 7. The user enters the case type identification in the Case Type ID field 80, the process type identification in the Process Type ID field 82 and the division identification 84, department identification 86, the workstation identification 88 and the workstation description 90 into the appropriate fields.

Figure 8:
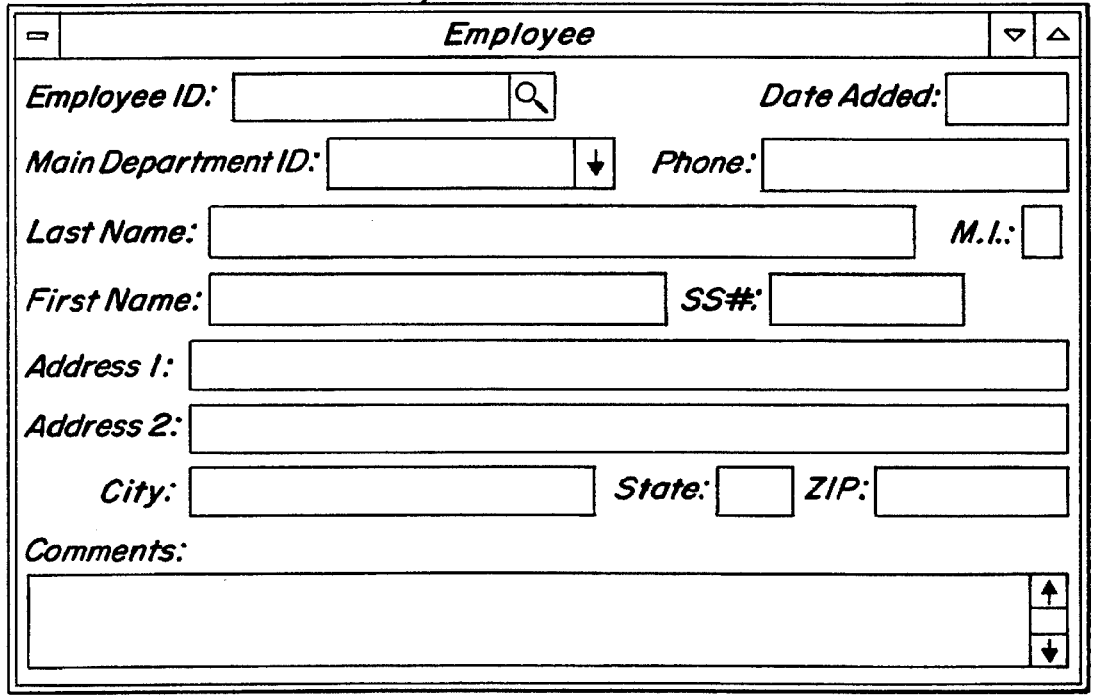
FIG. 8 is an illustration of one particular screen display, i.e., the Employee Form screen display, produced by the software forming a portion of the present invention.

The Employee Form 100 is displayed as shown in FIG. 8. In the Employee Form 100, the user can enter information about new employees or review and/or update information about existing employees that work in a department of a division of the dental laboratory. As shown in FIG. 8, the Employee Form 100 displays information including the employee's name, address, social security number, employee identification number, the department in which that employee works and other related information.

Utilizing additional forms, the system stores additional detailed information relating to the operation of the dental laboratory. On the Doctor Form 110, shown in FIG. 9, the user can input data pertaining to individual doctors who send work to the dental laboratory for processing. As shown in FIG. 9, the user can input data on the Doctor Form 110 including the doctor's full name, territory, license number, doctor's social security number and birth date, and terms of payment made by the doctor to the dental laboratory.

The Locations Form 120, shown in FIG. 10, is related to the Doctor Form 110. On the Location Form 120 the user can input or review information relating to the various office locations at which a doctor works including Doctor ID, doctor's full name, Location ID, location name, addresses, phone number, fax number, contact person's name, shipper's name, pick-up and delivery preferences, vacation start and end dates and comments. In this regard, it is not unusual for a doctor to conduct his own practice at a first office location, work for another doctor at a second office location and teach students at a university medical school where office facilities are provided by the university for the doctor's use. By utilizing this screen, user's of the system 5 may obtain information regarding each of a doctor's multiple offices.

By clicking on the Business Hours button 122 appearing in the lower right-hand corner of the Locations Form 120, the system 5 generates the Business Hours Form 130 as shown in FIG. 11. The Business Hours Form 130 enables the user to input or review information regarding the hours of operation for the various offices at which a doctor works as set forth in the Locations Form 20. The Business Hours Form 130 also enables the user to schedule the pick-up of cases from the doctor's office and delivery of processed cases to the doctor's office at times when the doctor is in at a particular office location.

On the Territory Form 140, shown in FIG. 12, the user can input information relating to the description of the territory assigned to particular dental laboratory drivers. The driver's identity may also be inputted on the form.

In circumstances where a doctor's office is beyond the territory of the dental laboratory, e.g., out of town, the laboratory typically ships cases to doctors and receives cases from doctors by means of any one of a number of outside courier services. The Ship Via Form 150, shown in FIG. 13, enables the user to record in the database information relating to the various outside couriers utilized by the dental laboratory for pick-up and delivery of cases. Such information includes the identity of the courier, telephone number, account number and comments including the type of shipping used, e.g., economy or overnight delivery.

Figures 13, 14:
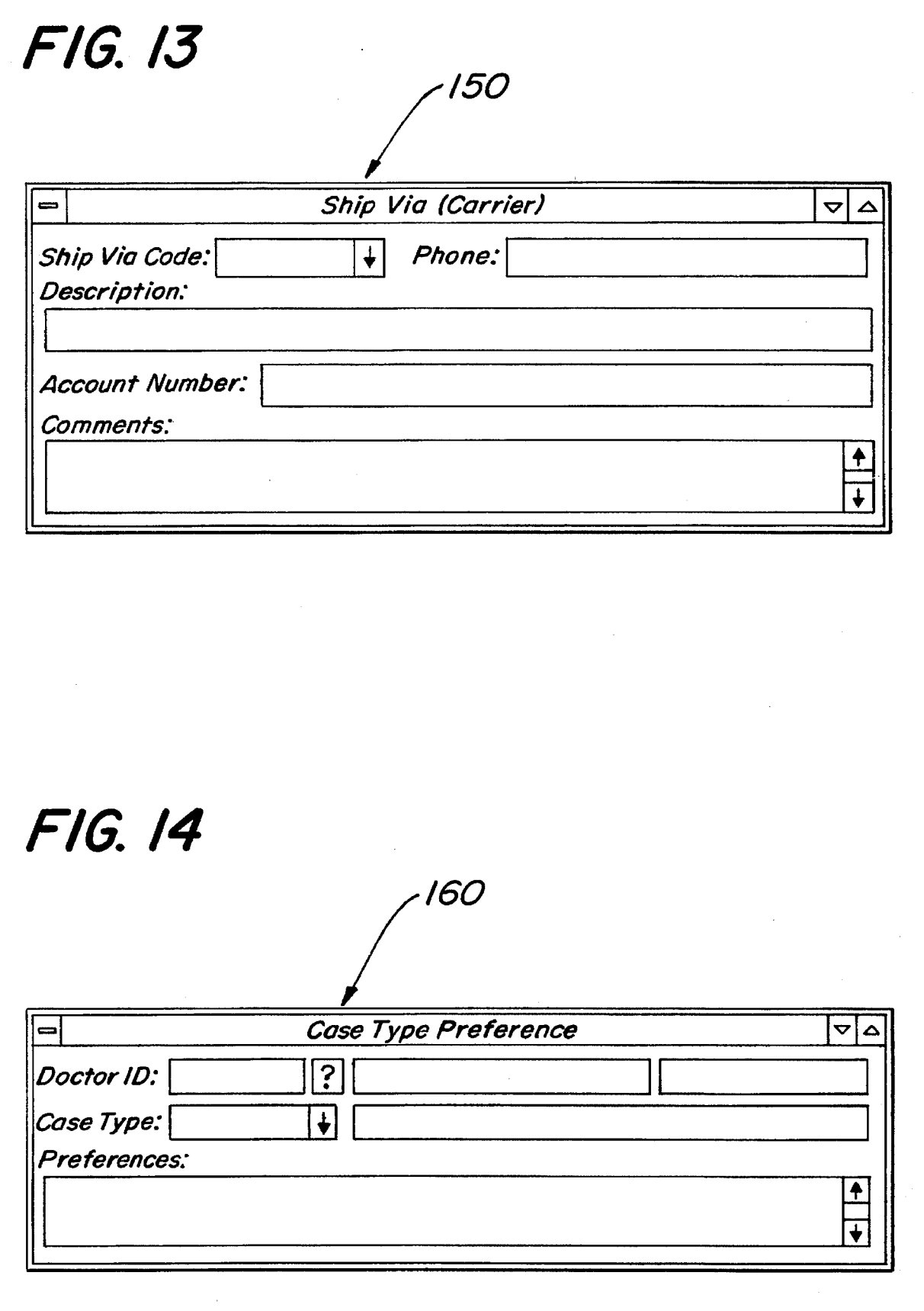

On another form, known as the Case Type Preferences Form 160, shown in FIG. 14, the user can input the preferences of individual doctors regarding the processing of their cases. For example, a dental laboratory is typically comprised of several departments. One department may perform all of the work relating to acrylics and another may perform all work relating to crowns. A third department may do all metal work and a fourth may do all the porcelain work. Particular doctors may have specific preferences regarding how they want their cases processed in one or several of these various departments. One doctor may prefer that crowns be prepared with a stippled surface, while another doctor may prefer a smooth finish. The system of the present invention is utilized to designate what preferences doctors desire with regard to the preparation of their cases, e.g., finishes on crowns.

Additionally, the Case Type Workstation Preferences Form 170, shown in FIG. 15, can be utilized by dental laboratory management to implement a doctor's preferences at a particular workstation. For example, in creating an acrylic denture, the case must be routed to a number of different workstations within the acrylic department where different steps in the manufacturing process are performed. In the system of the present invention, specific information regarding a doctor's preference regarding how work is performed on a case at a specific workstation may be provided to a technician.

Another form under the maintenance function is known as Moulds and Shades Form (not shown). The Moulds and Shades Form enables the user to specify the exact shading and mould of artificial teeth to be selected and used by technician during the preparation of dentures or crowns. The user makes the selection of moulds and shades in response to a doctor's prescription. This ensures that artificial teeth selected complement a patient's existing teeth in an aesthetically pleasing manner.

A Products Code Form 180, shown in FIG. 16, is utilized for the purpose of storing information about the various materials purchased by the dental laboratory and used in the preparation of cases. For example, in order to fabricate a denture, it is necessary for the dental laboratory to purchase various materials from outside manufacturers, such as artificial teeth, in order to build the denture. Cost information regarding these materials is stored on the Product Code Form 180 and includes product code, product description, Product Class ID, product price, raw material cost, part number, product manufacturer, billing information and product notes.

Utilizing the information inputted in the Product Code Form 180, the system 5 of the present invention generates a composite list of the various raw materials utilized by the dental laboratory in the preparation of cases and their associated costs. This information, i.e., the raw material and its associated cost, is contained in a product code bar code label. During the processing of cases, the product code bar code labels are scanned by the technician utilizing optical scanners to be discussed later in this application.

A Billing Codes Form 190, shown in FIG. 17, enables the user to determine the percentage of the total charge that a doctor will be charged for work performed by the laboratory. In some instances, for example, a doctor may return a case to the dental laboratory to be redone on the basis that the work initially performed by the laboratory is unsatisfactory as the result of poor workmanship or an original impression inaccuracy created by the doctor. In such instances, the dental laboratory may determine that it is appropriate to perform the rework, free of charge or for a percentage of the full amount to perform the work. The Billing Codes Form 190 enables the dental laboratory to generate a bill for any percentage, i.e., zero to one-hundred percent, of the full amount charged to the doctor.

The second general function performed by the system 5 of the present invention is the day-to-day management of the processing of cases in a dental laboratory. In processing cases, the system of the present invention performs a variety of tasks including the entry of case information into the system, the scheduling of work to be performed by technicians in the dental laboratory, the scheduling of case pick-ups from dentists' offices and the delivery of finished or partially finished cases to dentists' offices, the creation of invoices for completed work, maintenance, printing, driver routing, the posting of invoices to financial software packages and other functions.

Because much of the information needed to complete the forms associated with the processing of transactions has been previously input by case entry personnel during the set-up and maintenance function, minimal additional information needs to be inputted by the user during the day-to-day processing of transactions, thereby increasing efficiency. In other words, much of the information does not have to be re-keyed and will be displayed by the system 5 based upon previously completed forms during the maintenance function of the system 5.

The Case Entry Form 200 is displayed in FIG. 18. The Case Entry Form 200 is completed by case entry personnel when the dental laboratory initially receives a new case from a doctor and each time that case is returned to the dental laboratory for further processing.

As previously discussed, where a new case is being originated, the dental laboratory will receive materials from the doctor, such as an impression (in the case of a denture) and a prescription requesting that certain work be done, e.g., finish denture to first try-in stage. Upon receipt of those materials and prescription from the doctor's office, case entry personnel enter the necessary information onto the Case Entry Form 200.

On the Case Entry Form 200, the Creation Date field is automatically filled in with the current system date. As previously stated, much of the data entered into the fields on the Case Entry Form 200 is inputted by case entry personnel by clicking on various drop-down and zoom buttons appearing on the Case Entry Form 200 and making selections from system created lists, e.g., lists of Doctor ID, Case ID, Shades, Moulds, and Status. Additionally, case comments can be inputted here.

If the case is initiated for the first time, the system automatically assigns a new Case ID. To complete other fields on this form, the order entry clerk types the information directly into the field.

It is important to note that where a case is being originated, no information appears in the RX History Group Box 202. It is not until the RX Detail Form 220, shown in FIG. 20, is completed at least once by case entry personnel that information will appear in the RX History Group Box 202. The RX Detail Form 220 will be explained in detail below. Suffice it for now to say that each time the case is returned to the dental laboratory for further processing, case entry personnel will complete the RX Detail Form 220 by recording information relating to that particular iteration. Each time the RX Detail Form 220 is again completed, another line item of information is automatically added to the RX History Group Box 202 of the Case Entry Form 200.

It is also important to note that each time a case is returned for further processing and case entry personnel again complete the RX Detail Form 220, all process-related information inputted on previous RX Detail Form s 220 is retained and archived in the system 5 in order to create a database of information to be utilized by management.

In this regard, by simply looking at the number of entries made in the RX History Box 202 management can determine the number of iterations that have occurred for a particular case. Each line item in the RX History Box 202 represents a single iteration. The RX History Box 202 provides information including RX ID, Receipt Date, Ship Date and Remarks.

By monitoring iterations, management can reduce costs in ways previously discussed. By determining the number of iterations for particular case types, management can collect historical data and thereby establish an average number of iterations needed to finish particular case types. Cases that exceed the average number of iterations can be brought to management's attention and studied to determine the reason why the average number of iterations was exceeded. In one scenario where excessive iterations are identified, the doctor may have sent the case back for further processing as the result of unsatisfactory work performed by technicians. In this instance, corrective action, such as additional operator training may be necessary. In this manner, costs can be more aggressively reduced resulting in greater profits for the dental laboratory.

In another scenario, a particular doctor may habitually send work back to the dental laboratory to be redone despite the fact that the work was performed satisfactorily in the first place. The system 5 of the present invention enables the user to identify such doctors in order to reduce costs associated with unnecessary rework.

By clicking on the Teeth Button 208 appearing in the lower right-hand corner on the Case Entry Form 200, the system 5 generates a visual representation of the mouth, as seen in the Tooth Indicator Form 230 shown in FIG. 19. The Tooth Indicator Form 230 enables case entry personnel to utilize the mouse indicator 20 to indicate the areas or teeth on which work is to be performed in a particular case. Case entry personnel may also indicate whether a tooth is a pontic, i.e., an area where a tooth must be replaced, or an abutment, i.e., an area where a tooth has been cut down to support a crown or bridge.

By clicking on the RX Detail Button 204 from the Case Entry Form 200 (FIG. 18), case entry personnel can activate the RX Detail Form 220 shown in FIG. 20. The RX Detail Form 220 is utilized for several purposes. First, case entry personnel can specify the delivery location 212 and the delivery due date and time 214 requested by the doctor. Additionally, case entry personnel can specify the pan number 216 identifying the pan into which materials received from the doctor were placed and the actual date on which the completed case was return shipped 218 to the doctor. The Receipt Date field 220 of the RX Detail Form 210 is automatically populated by the system based upon the current system date. By clicking on the Remake Box 232 on the RX Detail Form 210, case entry personnel can designate whether the doctor's prescription calls for a remake. Each time the RX Detail Form 210 is completed, a new RX identification number is generated by the system 5 and an additional line of information is included in the RX (prescription) History Box 202 (FIG. 18). As previously stated, each time a new case is received by the dental laboratory and each time a case is returned for further processing, the RX Detail Form 220 is completed by case entry personnel. All information inputted on earlier RX Detail Form s 220 is preserved in system 5 rather than being overwritten.

By clicking on the RX Image button 234 appearing on the RX Detail Form 220, case entry personnel can view a computer generated image (not shown) of the paper prescription form filled out and sent to the dental laboratory by the doctor. The paper prescription sent in by the doctor must be first scanned into the system for the image to be generated.

By clicking on the Schedule Button 236 located on the RX Detail Form 210, case entry personnel can activate the Schedule Form 240 in order to schedule work to be performed in the dental laboratory for particular types of cases, e.g., crowns, bridges, implants, dentures, or partial dentures and based upon the stage toward completion. The Schedule Form 240 is shown in FIG. 21. Specifically, once a user has selected an appropriate case type and process type for a particular case, the system automatically populates several of the boxes within the Workstations Box of the Schedule Form 240 with information relating to the processing of that case.

This system generated information contained within the Workstations Box includes the sequence of process steps, the various workstations at which these steps will be performed, the estimated start time, estimated finish time, actual start time and actual finish time. The estimated start and finish times are based upon predetermined estimates inputted in the system during set-up and maintenance. The relationships between case types, process types and workstations has been previously established in the system by completion of forms during maintenance, e.g., the Case Types Form 58 shown in FIG. 5 and Case Types To Process Types To Workstation Links Form 78 shown in FIG. 7.

By clicking on the Print Labels Button 242 on the RX Detail Form 210, the system 5 generates a work ticket 248, a shipping label 250 and an RX (prescription) return form 252 as shown in FIGS. 22A through 22E.

A new work ticket 248, shipping label 250 and RX (prescription) return form 252 is generated each time a new case is received by the dental laboratory and each time a case is returned to the dental laboratory for further processing. The work ticket 248, shipping label 250 and RX return form 252 remain with the case during all processing steps.

Referring to FIG. 1, the work ticket 248, shipping label 250 and RX (prescription) return form 252 are printed on a dedicated bar code printer 10 located within network 6. It is preferred that thermal printers or laser printers be utilized for the printing of labels containing bar codes in the present system rather than dot matrix printers because thermal or laser printers render a higher quality more readable bar code than dot matrix printers. Bar coded data described in this disclosure is configured in accordance with Code 128 which is a standard bar code symbology.

Figure 22B:
FIG. 22B is a pictorial representation of a second portion of the work ticket used in accordance with the present invention.
Figure 22C:
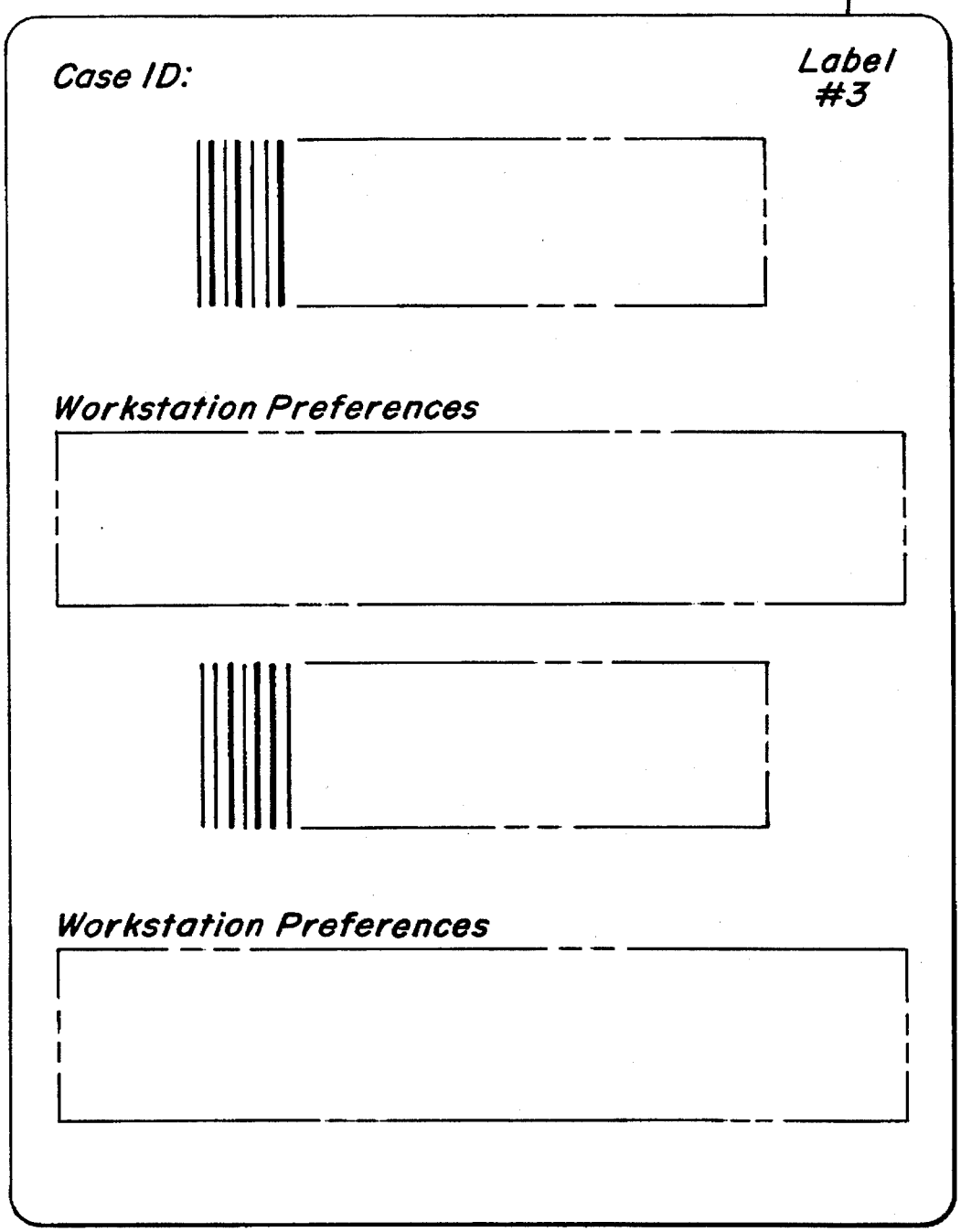
FIG. 22C is a pictorial representation of a third portion of the work ticket used in accordance with the present invention.

As shown in FIGS. 22A through 22C, the work ticket 248 of the present invention is shown as comprising three labels: Label #1 shown in FIG. 22A, Label #2 shown in FIG. 22B and Label #3 shown in FIG. 22C. Each label of work ticket 248 contains various types of information. However, it should be understood that the information contained on Label #1, Label #2 and Label #3 of work ticket 248 could be combined and contained on a single work ticket 248 for the purpose of convenience and simplicity.

As shown in FIG. 22A, Label #1 of the work ticket 248 displays information including Doctor ID, Doctor's Name, Case ID, RX ID, Case Type ID, Process Type ID, Division ID, Department ID, Pan No., Creation Date, Receipt Date, Due Date, Case Comments, RX Comments, Material Comments and Case Type Preferences.

As shown in FIG. 22B, Label #2 of the work ticket 248 displays the Doctor ID, Doctor's Name, materials received from the doctor's office, and a bar code label containing the Case ID and RX ID information.

As shown in FIG. 22C, Label #3 of the work ticket 248 contains two bar code labels. Each bar code label contains the Workstation ID of a different workstation at which work is to be performed by a technician. It should be understood that Label #3 can contain one or more bar codes depending upon the number of workstations at which work must be performed when a case is sent to the dental laboratory for processing.

For example, a case may be sent to the dental laboratory by the doctor's office for processing including articulation, wax-up and finishing. Each of these processing steps is performed at a different workstation having a different Workstation ID. Since the case is going to be processed at three workstations, prior to processing, the case entry personnel would prepare Label #3 to contain three bar codes: one designating the Workstation ID for articulation, one designating the Workstation ID for wax-up and one designating the Workstation ID for finishing.

Once the case has been received at the articulation workstation, the technician passes an optical scanner 253 to be explained in further detail below, over the bar code found on Label #2 in order to input the Case ID and RX ID into the system 5. Next, the technician passes the optical scanner 253 over the bar code found on Label #3 designating the Workstation ID for articulation, to signal to the system that the articulation step has begun. This is known as a start process scan. Once the articulation step has been completed, the technician will again pass the optical scanner 253 over the bar code found on Label #3 designating the articulation workstation to signal to the system that the articulation step has been completed. This is known as an end process scan.

The case is then transferred to the wax-up and finishing workstations where the identical bar code scanning procedure is followed.

Information contained on Label #1, #2 and #3 of work ticket 248 has been previously specified by case entry personnel during completion of forms previously discussed, e.g., the Case Entry Form 200 shown in FIG. 18 and the RX Detail Form 210 shown in FIG. 20.

The RX (prescription) return form 252, shown in FIG. 22D, is generated by case entry personnel each time the case is returned to the dental laboratory for additional processing. Once the RX (prescription) return form 252 is generated, it is accumulated with the case and remains with the case during processing and stays with the case when it is shipped to the doctor's office.

As shown in FIG. 22D, the RX return form contains specific information about the case including the return address of the dental laboratory, the Division name, Doctor name, Case ID, RX ID, Patient Name and Preferences. This information is printed on the RX Return form and is also contained in a bar-code label that appears at the top of the RX return form 252.

The RX (prescription) return form 252 is provided with an adhesive back and is intended to be affixed by doctor's office personnel to the exterior of the shipping box containing the case when the case is returned to the dental laboratory for additional processing. When the case is received by the dental laboratory, information relating to said case can easily be inputted into system 5 by case entry personnel by scanning the bar code located at the top of the RX (prescription) return form 252.

It is important to note that scanning of the RX return form 252 signals to the system 5 that another iteration has occurred. In other words, each time an RX return form 252 is scanned for a particular case, a new line appears under the RX History Box 202 of the Case Entry Form 200 shown in FIG. 18.

The Shipping Label 250 shown in FIG. 22E, is created by case entry personnel once a case is received by the dental laboratory. The Shipping Label 250 is intended to be utilized by the dental laboratory for shipping the case to the doctor's office after completion of processing. The Shipping Label 250 contains a bar code encoded with information relating to the case. Once the Shipping Label 250 has been scanned, along with all other previous scans, the system is alerted to the fact that the case is ready to be shipped.

Referring again to FIG. 1, in accordance with the present invention, hand-held optical scanners 253 are utilized by technicians to read the previously mentioned bar code labels contained on work tickets 248, return labels 252 and shipping labels 250 for recording vital information during the processing of cases through the dental laboratory. One such hand-held optical scanner particularly suited to perform the function of scanning bar codes is sold under the name Microwand III Interface Hand-Held Bar Code Scanner manufactured by Hand Held Products, Inc, model number 32ES.

The hand-held optical scanner 253 is provided with an 80386 microprocessor or faster, 512 kilobytes of memory or more and software (hereinafter referred to as the "scanner software") enabling the scanner 253 to collect data from the various bar codes previously described in this disclosure, e.g., work tickets 248, RX (prescription) return labels 252 and shipping labels 250 and to upload said data to the server 116 in a flat ASCII form at using a standard communications protocol. The scanner 253 uploads data to the server 116 by means of a docking station 260. The scanner 253 is also provided with rechargeable batteries so that it can be portable and therefore may be utilized at various workstations within various departments of the dental laboratory.

The scanner 253 is provided with a liquid crystal display (LCD) which displays information prompting a user to input specific information by scanning or keying.

In accordance with the present invention, the scanner software enables the scanner to collect data scanned by various technicians and keep separate in its memory data collected by each of those multiple technicians. This capability makes it unnecessary to provide each workstation in the dental laboratory with its own dedicated scanner. In accordance with the present invention, one or several of these scanner 253 are positioned within each of the departments in the dental laboratories, e.g., production, inspection and shipping and receiving.

Figure 26:
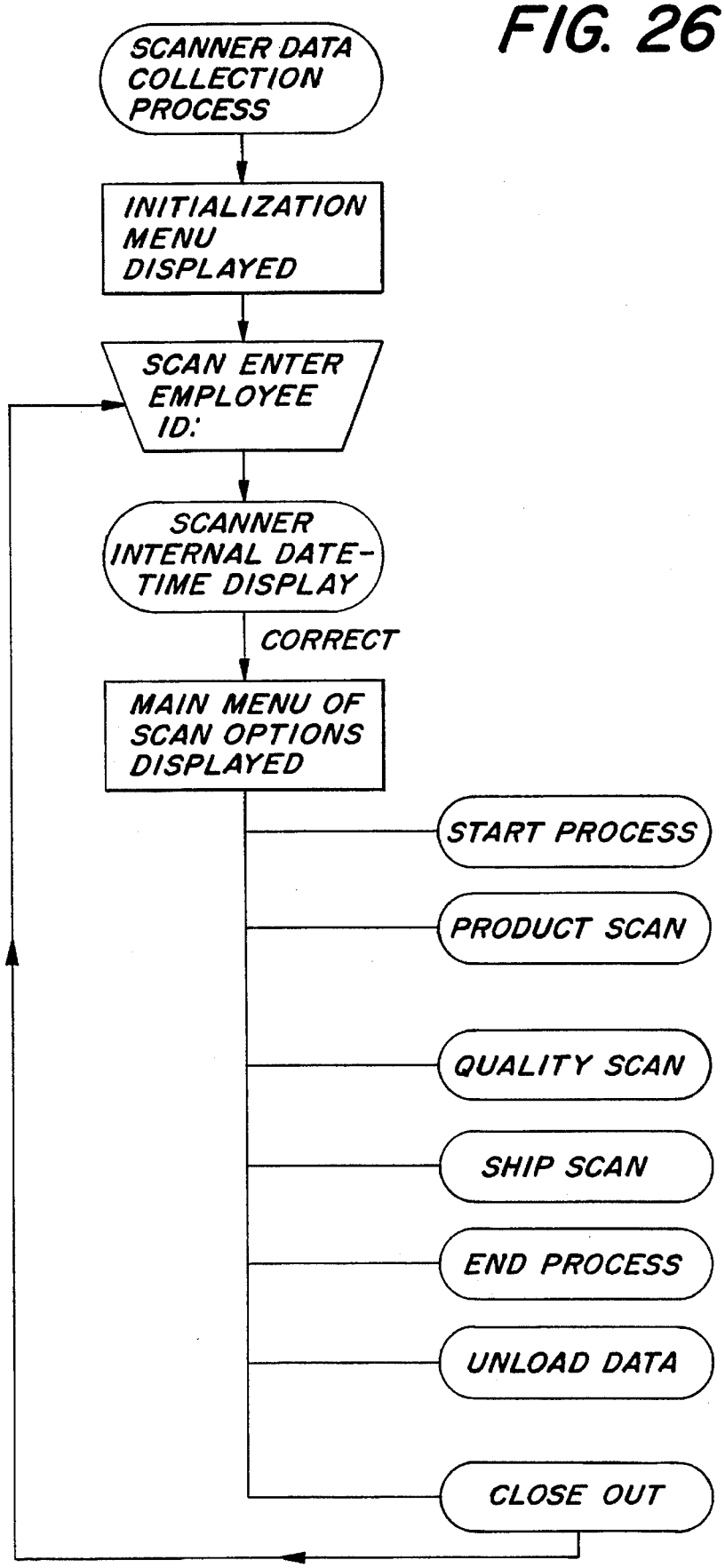
FIG. 26 is a flow chart illustrating the operation of a bar-code scanner used in accordance with the present invention.

Referring now to FIG. 26, the scanner software enables the scanner .253 to perform seven types of scans: a start process scan, a product scan scan, a quality scan, a ship scan, an end process scan, an upload data scan and a close out scan.

As shown in FIG. 26, the scanner will first display an initialization menu prompting the technician to input his or her identification number. The technician may input the employee identification number by scanning or alternatively, the technician can key this information into the system 5 manually. Once the technician's employee identification number is inputted, the scanner 253 displays the internal date and time. The accuracy of the date and time is to be verified by the technician before performing any scans. Each time a technician perform s a scan, the scanner software will automatically associate with that scan the exact time and date at which the scan was perform ed.

Once the technician has verified the accuracy of the internal time and date displayed on the scanner 253, the scanner will display a menu of scan options including: start process scan, product scan, quality scan, ship scan, end process scan, upload data scan and close out scan. The operator perform s a start process scan upon beginning work on a particular job and an end process scan when the work has been completed at that particular workstation.

The start process scan consists of two modes, single case and batch mode. As should be appreciated by those skilled in the art, in the dental laboratory, certain processes may be perform ed more efficiently by processing groups of cases simultaneously in batch mode rather than sequentially. One such operation, e.g., the pouring of stone or plaster into impression trays to create plaster models, may be perform ed more efficiently by preparing an amount of stone or plaster to be poured into a batch of cases rather than preparing a new amount to be poured into each case individually.

In the single case mode, the scanner 253 will prompt the technician for Case ID and RX ID then workstation information which will be time and date stamped. Batch case mode will enable the scanner 253 to scan multiple cases until ended by a key press. This information is then time and date stamped.

The end process scan is identical to the start process scan and is perform ed when processing has been completed at a particular workstation. The scanner 253 is equipped with internal software enabling it to keep track of elapsed time between the start process scan and the end process scan. The scanner 253 gathers start process, end process, elapsed time, Case ID and RX ID under a scan serial number and stores this information in the internal memory of the scanner 253.

The product scan function will prompt for the Case ID and the RX ID to be scanned then the product code and the bill code. All data to be collected can be scanned or manually entered. The quantity is then entered. If the product is a metal, the scanner will prompt for a weight value after the quantity is entered. The scanner 253 then internally dates and time stamps and stores the product scan. Each of the various product codes are found on a set of bar code labels in a binder located at the operator's workstation.

Once processing on a case has been completed, it is sent to quality control for inspection. If that particular case passes inspection, the quality control operator perform s a quality control scan, i.e., the inspector waves the scanner 253 over a bar code (not shown) to indicate the case has passed quality control inspection and is ready for shipping.

After the quality control scan is completed, the case moves to shipping. The shipping scan is perform ed by scanning the bar code contained on the Shipping Label 250 described above. Once the Shipping Label 250 has been scanned, the case is considered ready to be shipped.

As shown in FIG. 26, before a second technician may utilize the scanner 253 to perform scans, the first technician must perform a close out scan to terminate that technician's session. By performing the close out scan, the first technician resets scanner 253 for use by the second technician. Thereafter, a second technician can perform scans as previously described. When the second technician obtains the scanner 253 he will be instructed to first enter his or her employee identification number before performing any scans. The scanner 253 will also be closed out prior to uploading any information to the database on system 5. This will ensure that scanned data will remain associated with the proper technician.

At the end of each workday or during the day, each scanner 253 is attached to a docking station 260 as shown in FIG. 1. The purpose of the docking station is to facilitate the uploading of data collected by the scanner 253 during the day into the database located on the server workstation 16. The docking station 260 is often a microcomputer, e.g., personal computer. Microcomputers utilized as docking stations 260 in accordance with this invention preferably possess an 80486 type microprocessor or faster and between eight and sixteen megabytes of random access memory. Each day, the workstation server 16 incorporates those scanner 253 scans perform ed that day with existing information on the database.

It is important to note that the various scans that are perform ed using the scanner 253 as the case is processed in the dental laboratory are archived in the database of the system 5 rather than being overwritten.

The various scanner 253 scans perform ed throughout the processing of a case are displayed on the Scan Maintenance Form 280 shown in FIG. 23. By entering search criteria, i.e., Case ID, Scan Type, Department ID, Employee ID and date range, and clicking on Search 281, the system enables the user to determine the status of a case by reviewing the scans perform ed. The Scan Maintenance Form 280 lists information relating to each scan perform ed on a particular case including the scan type, the date on which the scan was perform ed, the department where the scan was perform ed, the identification of the employee that perform ed the scan. In this manner, management can determine the location of any case on the laboratory floor at any particular time. Therefore, the Scan Maintenance Form 280 serves as a tool for management to determine how close to completion a particular case is and tells management what workstation and operator are presently working on the case. In response to a doctor's request, the laboratory can determine whether that doctor is going to receive the case from the dental laboratory by the date requested.

The user can access the Workstation Logging Form 290, shown in FIG. 24 from the maintenance menu. By entering search criteria, i.e., Division ID, Case ID, RX ID, Case Type ID, Workstation ID, and Employee ID, the system will display in the Time Spent Box 291 the elapsed time taken by an identified operator to complete a specific task on the shop floor. The elapsed time provided by the system 5 provides a tool for management to review the actual elapsed time for technicians to perform specific tasks in the dental laboratory.

By keeping historical records of elapsed times and utilizing statistical methods, management can establish control parameters or average times. An operator's performance can be compared against these control parameters to determine whether that operator is performing exceptionally, satisfactorily or unsatisfactorily. Instances where an operator's time falls below the established control parameters can be identified by management and corrective action can be taken where necessary. Such corrective action may include additional operator training or the conducting of studies to determine improved methods. The use of scientific management techniques will increase productivity. Finally, by determining actual process times for each case type, management is able to determine labor costs and therefore can more effectively determine pricing.

The Schedule Pick-up and Delivery Form 194 is displayed in FIG. 17a. The purpose of the Schedule Pick-up and Delivery Form 194 is to enable the entry of numerous details regarding the doctors' requests for pick-up and delivery of his or her cases. Scheduled pick-ups of cases from the doctor's office can be initiated by the doctor calling the dental laboratory or pick-ups can be scheduled in the system to be recurring at specific times and days. The Schedule Pick-up and Delivery Form 194 is also utilized by the dental laboratory to ship finished or partially finished cases back to the doctor's office. The Schedule Pick-up and Delivery Form 194 is completed by clicking on the various drop-down buttons located on the form and making selections for the various parameters set forth on the form, e.g., Division ID, Doctor ID, Location ID, Case ID, RX ID, Ship Via, Territory, Estimated Arrival Time, Requested Arrival Time. However, shipping is automatic based upon the case delivery date specified by the doctor.

Figure 25:
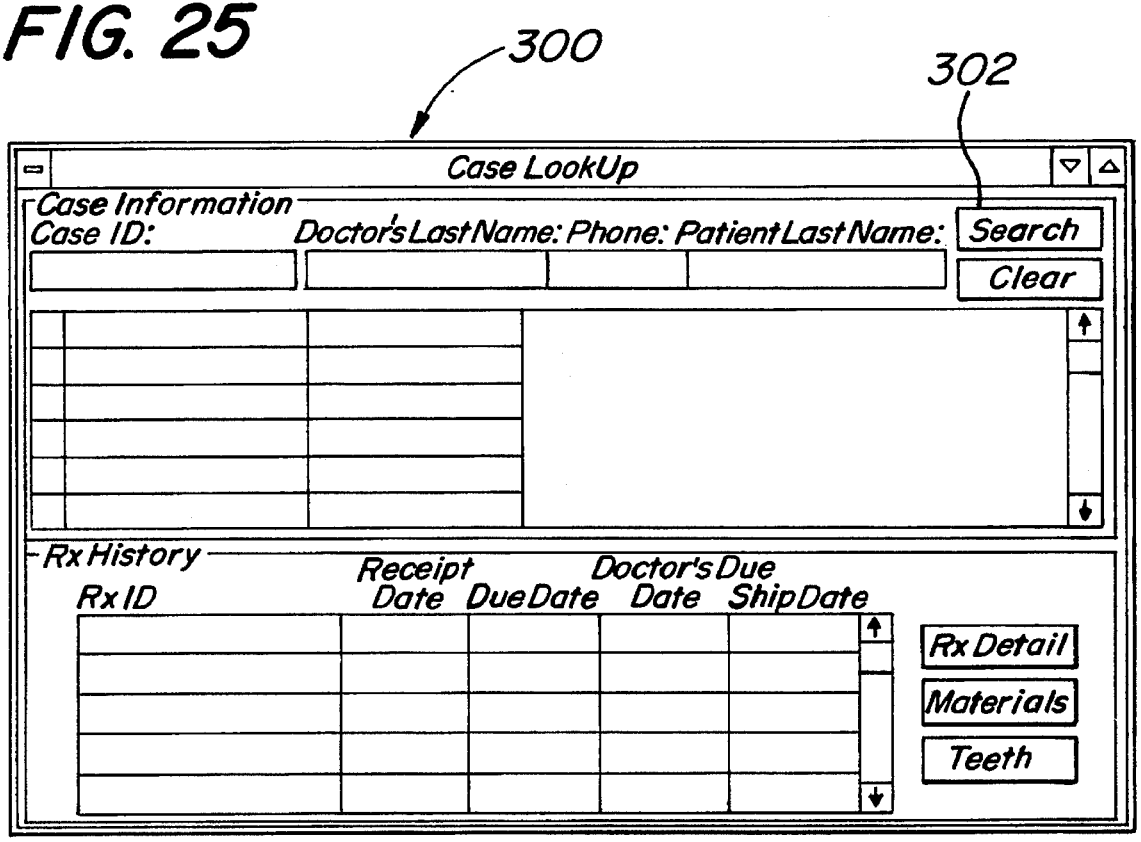
FIG. 25 is an illustration of one particular screen display, i.e., the Case Look-up Form screen display, produced by the software forming a portion of the present invention.

The Case Look-up Form 300 is shown in FIG. 25. A doctor may obtain limited access to the system of the present invention by means of connection through a computer and a modem line. Doctors may utilize the Case Look-up Form 300 to determine the status of cases they have sent to the dental laboratory for processing. The doctor may enter search data such as the case identification, doctor's last name, doctor's telephone number, patient's last name or any combination and clicking the Search Button 302 to search for a desired case. Boxes contained within the Case Look-up Form 300 are then populated by the system that match the search criteria with the most recent case being highlighted. The doctor can then select a different case if desired. Once the desired case is selected, the user can view the prescription history by clicking on RX Detail (previously described).

Doctors utilizing the Case Look-up Form 300 can also specify preferences.

Without further elaboration, the foregoing will so fully illustrate my invention that others may, by applying current or future knowledge, adapt the same for use under various conditions of service.

I claim:

1. A system for managing the processing of dental appliances being fabricated in a dental laboratory wherein the fabrication of such appliances is achieved in iterations, with the first of said iterations comprising receipt of a prescription from the doctor for fabricating the appliance therefrom, and with subsequent iterations comprising return of the appliance by the doctor to the laboratory for additional processing, said system comprises digital processing means, a data collection means, and data storage means, said data collection means being arranged to collect process related data associated with each iteration, data storage means being arranged to store said process related data associated with each iteration while preserving previously stored data associated with prior iterations, whereupon data indicative of the history of the fabrication of the appliance through all of the iterations is available to the operator of the laboratory for analysis and the effective and efficient management of the laboratory, said data collection means comprising a bar-code scanner and wherein said system additionally comprises a work ticket, a prescription return form and a shipping label, each having at least one bar-code label containing said process related data and readable by said bar-code scanner.

2. The system of claim 1 wherein said bar-code label of said work ticket contains information identifying the workstations at which processing steps are to be performed.

3. The system of claim 1 wherein said bar-code label of said prescription return form contains doctor identification, case identification, and prescription identification.

4. The system of claim 1 wherein said bar-code label of said shipping label contains a doctor's identification and shipping address.

5. The system of claim 1 wherein said system additionally comprises a bar code printer and wherein said work ticket, prescription return form and shipping label are printed on said bar-code printer.

6. The system of claim 5 wherein said bar-code printer is a laser printer.

7. The system of claim 5 wherein said bar-code printer is a thermal printer.

8. The system of claim 1 wherein the dental laboratory includes a plurality of divisions.

9. The system of claim 1 wherein said bar-code scanner is hand-holdable.

10. The system of claim 9 wherein said bar-code scanner is portable.

11. The system of claim 1 wherein said digital processing means comprises a server workstation and plural client workstations, said client workstations being located within selected departments of the dental laboratory.

12. The system of claim 11 wherein said data collection means comprises a bar-code scanner capable of serving said plural client work stations.

13. The system of claim 12 wherein said bar-code scanner is capable of processing data in batch mode.

14. The system of claim 12 wherein said bar-code scanner is capable of processing data in single case mode.

15. The system of claim 12 wherein said bar-code scanner contains a microprocessor and memory for storing said process related data.

16. The system of claim 11 wherein said system additionally comprises a network, said network comprising a communication channel connecting said server workstation with at least one said client workstation.

17. The system of claim 16 wherein said client workstation is a microcomputer.

18. The system of claim 12 wherein said server workstation is a microcomputer.

19. The system of claim 1 wherein said data storage means comprises a relational database.

\* \* \* \* \*